United States Patent
Kolari

Patent Number: 5,808,734
Date of Patent: Sep. 15, 1998

[54] METHOD AND APPARATUS FOR DETECTING IMPURITIES ON PLATE SURFACE

[76] Inventor: Matti Kolari, Mustikkakuja 8, FIN-04200 Kerava, Finland

[21] Appl. No.: 619,665
[22] PCT Filed: Mar. 2, 1995
[86] PCT No.: PCT/FI95/00119
§ 371 Date: Aug. 26, 1996
§ 102(e) Date: Aug. 26, 1996
[87] PCT Pub. No.: WO95/24635
PCT Pub. Date: Sep. 14, 1995

[30] Foreign Application Priority Data
Mar. 9, 1994 [FI] Finland ................................. 941098

[51] Int. Cl.⁶ .................. G01N 21/43; H02P 1/04
[52] U.S. Cl. ............ 356/237; 250/341.8; 318/444; 318/480; 318/DIG. 2
[58] Field of Search ............ 356/237; 318/443, 318/444, 480, DIG. 2; 250/341.8

[56] References Cited

U.S. PATENT DOCUMENTS

| | | |
|---|---|---|
| 3,947,131 | 3/1976 | Karl . |
| 4,701,613 | 10/1987 | Watanabe et al. .................. 250/341.8 |
| 4,798,956 | 1/1989 | Hochstein .............................. 250/341.8 |
| 4,871,917 | 10/1989 | O'Farrell et al. . |
| 4,960,996 | 10/1990 | Hochstein ............................. 250/341.8 |
| 5,015,931 | 5/1991 | Muller . |
| 5,483,346 | 1/1996 | Butzer .................................... 356/369 |

FOREIGN PATENT DOCUMENTS

WO 91/03393  3/1991  WIPO .

Primary Examiner—David C. Nelms
Assistant Examiner—Zandra V. Smith
Attorney, Agent, or Firm—Dilworth & Barrese

[57] ABSTRACT

The present invention relates to a method and apparatus for selective measurement of liquid and solid particles deposited on plate surfaces. The method is based on the transmission of radiation, which originates from total reflection from the interface between liquid droplets at the surface of the plate and surrounding gas, e.g., air. This radiation is transferred inside the plate as radiation undergoing total internal reflection between the surfaces of the plate. Such measuring radiation reaches a detector protected from background radiation, whereby intensity increase can be measured and used for the control, e.g., windshield wipers and washer equipment.

15 Claims, 3 Drawing Sheets

METHOD AND APPARATUS FOR DETECTING IMPURITIES ON PLATE SURFACE

BACKGROUND OF THE INVENTION

The present invention relates to a method and an apparatus for detecting impurities on the surface of a plate transparent to electromagnetic radiation. A particular object of the invention is to provide a method and an apparatus for detecting water and/or solid dirt on the windshield of a vehicle and a demand-based control system based on the method for automatic starting and stopping of a windshield wiper and washer.

In practice a plurality of needs arise for measuring the portion of the area covered by impurities on the surface of a plate. In a great number of such applications the measurement need not be particularly accurate, but rather, simple and reliable function in harsh and varying conditions is required. Typically, a plate surface on which the relative area covered by liquid and/or solid dirt is desired to be measured is the windshield or rear window of a vehicle, working machine or similar equipment. Reliable measurement in such an application permits the automatic control of the windshield wipers and washer equipment.

Several tens of inventions intended to solve the above-described vehicle control application have been filed. However, their commercial use in vehicles has not been implemented. This situation is the result of technical deficiencies in these solutions.

In the prior art four different types of solutions have been proposed based on change of capacitance, refraction and reflection of electromagnetic radiation (mostly infra-red and visible light), reflection of microwaves, and acoustic emissions from the impact of raindrops. Under varying conditions (of humidity and temperature), the capacitive methods fail to achieve sufficient accuracy under conditions of low humidity. A majority of the disclosed inventions are based on the utilization of different types of reflection or refraction of electromagnetic radiation. In fact, this currently seems to offer the only viable solution to achieve a sufficiently sensitive, uncomplicated and reliable embodiment for varying conditions.

Embodiments based on electromagnetic radiation can be categorized into two major classes: in one group the radiation is transmitted from inside the glass via an air gap and the radiation is reflected/backscattered at the water droplets and/or solid dirt deposited on the surface of the glass. In the other group the radiation is transmitted to the inside of the glass via a prism at an angle which makes the radiation undergo total reflection during its propagation in the glass. The inventions of the latter type are mostly based on the principle disclosed in the Swedish Pat. No. 353,497 filed in 1969. According to this invention, radiation transmitted into the glass via a prism propagates undergoing total reflection at alternate surfaces of the glass. A fraction of the radiation is routed out from the glass with the help of another prism after a few incidents of total reflection. If the radiation at the point of total reflection meets a water droplet on the glass surface, it can exit the glass. This causes a reduction in the intensity taken out through the receiving prism, whereby intensity reduction can be used to detect the existence of water droplets on the glass surface.

The method according to cited Swedish patent-has a crucial and essential shortcoming in that the intensity variations of background radiation are excessively large with respect to the measured effect. Resultingly, a detector which is sufficiently sensitive to measure the intensity variations caused by the desired effect will be overloaded (saturated) at extreme levels of background radiation such as, e.g., direct sunlight. In this situation the system functions are inhibited. The same shortcoming applies to almost all inventions employing this principle. An exception to this is described below.

Among other shortcomings, inventions based on the intensity measurement of returning radiation by means of a detector surrounded by free air are hampered by the same problem described above (that is, overloading of a sensitive detector), which makes them usable under specific conditions only that are rarely realized.

U.S. Pat. No. 4,676,638 discloses a solution to this problem. According to this invention, two different methods are employed to prevent the background radiation from reaching the detector. The first method is to use a multifaceted prism of such a geometry in which the background radiation after a first total reflection at the surface of the prism along its path is directed to impinge on a nonreflective surface. This is not the case with the radiation used for the measurement which radiation is arranged to travel via a second reflection inside the prism to a photodetector. Another embodiment according to the same patent for separating the background radiation employs the same principle. Using a rectangular prism and an air gap, this embodiment subjects the background radiation to total reflection at the back face of the prism thus preventing it from reaching the photodetector. This arrangement can be accomplished by means of a rectangular prism owing to the advantageous compatibility of the refractive indices of glass, water and air as is evidenced in great detail in the patent text. Also this patent is based on the principle originally disclosed in the Swedish patent cited above.

The embodiment described in cited US patent has a number of shortcomings. One important drawback is related to the tight tolerance requirements set for the prism-transducer combination and its mounting. According to the US patent, the prisms must be manufactured to extreme accuracy as to their faces and angles to avoid the background radiation from reaching the transducer in the form of stray rays caused by incorrect angles or excessive roughness of surfaces. Furthermore, the gratings to be placed in the air gaps must have very high dimensional accuracy and their placement must be carried out with extreme precision. Moreover, successful practical application of the apparatus according to the invention presumes individual and accurate fabrication of the prism and the gratings according to the windshield thickness.

In an apparatus according to DE Pat. No. 4,229,491 the radiation employed for measurement is transmitted to the inside of the windshield glass via a transparent piece attached to the glass without an air gap. The radiation is transmitted into the glass at an entrance angle that causes the radiation to undergo total internal reflection at the opposite internal surface of the glass and become extinct on a nonreflective stop placed on the entrance surface. However, a fraction of the radiation may possibly reach a water droplet on the surface of the glass, whereby it is partially reflected also to the inside of the glass from the droplet. A fraction of the radiation undergoing total internal reflection at the inside of the water droplet is transmitted through the glass at such an angle that avoids becoming blocked by the nonreflective stop. The detector for the reflected radiation is placed inside the glass at a suitable angle which permits the detector to capture a fraction of the radiation reflected by the water droplets. The intensity of the radiation captured by the detector increases in proportion to the amount of water droplets on the surface of the glass. Accordingly, the detector of this invention is placed in free air. Although the placement of the detector can be selected relatively well protected from background light, in vehicle use the detector will be subjected to background light and its variations, which is the case for almost all of the prior-art inventions as noted above.

In general, all embodiments based on conventional techniques require a great number of transmitter/receiver components in order to make the signal range sufficiently wide to give a reliable result also for small amounts of measured impurities. This increases production costs, and with regard to measured area, the size of the detector unit becomes excessively large for use in vehicles, for instance.

SUMMARY OF THE INVENTION

It is an object of the present invention to generally achieve a method and an apparatus capable of overcoming the disadvantages of the above-cited patents and embodiments based on prior-art techniques. Accordingly, it is a particular object of the invention to provide a method and an apparatus characterized in that the photodetector is protected from background radiation and is selective with respect to water and solid dirt, whereby a single apparatus is capable of detecting the existence of both water and dirt on, e.g., a vehicle windshield irrespective of varying external conditions such as illumination variations related to day and night conditions and lights of meeting vehicles. Accordingly, the invention makes it possible to implement the automatic control of both the windshield wipers and washer equipment. Another particular object of the invention is to provide a method and an apparatus capable of measuring over a large area without increasing the size of the detector (detector piece glued to the glass) as according to the invention the extent of the measured area is dependent only on the area illuminated by the measuring radiation. A still further particular object of the invention is to provide a method and an apparatus for the automatic control of a vehicle windshield wiper and washer equipment thus dispensing with the need for conventional multistage wiper switches and timers as well as multispeed wiper motors. Resultingly, the application of the invention to a new vehicle possibly lowers the overall cost over conventional techniques, while simultaneously the embodiment is safer, easier and more economical in use. Traffic safety is improved significantly, since the driver can concentrate on driving as good visibility is automatically maintained even during rapid changes in traffic situations including passing a vehicle, meeting another vehicle on dirty or sloshy roads, etc.

According to the present invention, the above-mentioned goals are accomplished by a method of detecting liquid and/or dirt on the surface of a plate. In which method radiation emitted by at least one source of electromagnetic radiation is transmitted to propagate totally reflected in the inside of said plate and is received by at least one detector sensitive to said electromagnetic radiation, whereby the presence of liquid and/or dirt on the outer surface of said transparent plate is detected in the form of an intensity change of the radiation received by said detector. The method according to the invention is characterized in that the source of radiation is placed relative to the plate surface so that the radiation emitted by the source is transmitted through the plate when the plate surfaces are dry and/or clean, but water droplets and/or dirt deposited on the surface of the plate cause at least a fraction of the radiation to be reflected back to the inside of the plate and thus becoming partially transmitted forward in the inside of the plate in the form of radiation undergoing total internal reflection at the plate surfaces until reaching the detector and is there detected as the intensity increase of the received radiation.

The invention also provides an apparatus for detecting liquid and/or dirt on the surface of a transparent plate, in which apparatus radiation emitted by at least one source of electromagnetic radiation is transmitted to propagate in the inside of said transparent plate by total reflection from the surfaces of the plate, whereby the presence of liquid and/or dirt is detected in the form of an intensity change of the radiation. The apparatus according to the invention is characterized in that the apparatus comprises at least one radiation emitting element placed close to the surface of the plate so that the radiation emitted by the element is transmitted through the plate when the plate is dry and/or clean, while at water droplets and/or dirt deposited on the surface of the plate, at least a fraction of the radiation is reflected back to the inside of the plate and thus partially transmitted forward within the plate by radiation undergoing total internal reflection at the plate surfaces, and that the apparatus further comprises radiation receiving elements adapted to receive/detect the radiation propagating within the plate in the form of totally reflected radiation and to sense liquid and/or dirt deposited on the surface of the plate from the detected intensity increase of the received radiation.

The operating principle of the invention is essentially based on transmitting the measuring radiation via free air onto the measured area of the surface of the plate, whereby the radiation will be entirely transmitted through the plate if the radiation is not incident on any obstacles to be measured, while obstacles such as water and dirt deposited on the plate surface cause the radiation to be reflected back to the inside of the plate thus permitting the radiation to propagate inside the plate by total internal reflection from the surfaces of the plate finally reaching the detector. In this fashion even a small transducer can be adapted to measure over a large plate area as the measured area in fact covers the plate surface as widely as is illuminated by the measuring radiation. In embodiments of conventional techniques based on transmitting the measuring radiation onto the glass via a prism, for instance, the measured area as well as the intensity of light radiation available for measurement with respect to the background radiation intensity remain very small. A further essential property of the present invention is that the measuring radiation is separated from the background radiation by means of an aperture stop which allows the detector to be illuminated only by radiation entering at an angle resulting from total internal reflection. In contrast to inventions based on transmitting the measuring radiation onto the glass by means of a prism or similar element, the present invention requires no accessory elements at the measured area.

The method according to the present invention can be applied to both sensing liquid droplets such as water droplets on the surface of a transparent plate and detecting dirt-containing droplets on the surface of a plate. For the former purpose the source of radiation is aligned with respect to the measured plate surface so that the angle $\beta 1$ of the measuring ray to the plate surface toward the detector element is in the range 90°–180°. The rays which are incident at angles falling within this range will escape through the glass if dry. When water droplets are deposited on the plate surface, a fraction of the rays escaping through the glass, which fraction is dependent on the entrance angle of the rays and the shape of the water droplets, will be incident on the interface between the water droplet and air at such an angle that the rays will be returned by total internal reflection back so as to re-enter the glass at an angle with respect to the glass surface that again subjects the ray to total internal reflection. The rays propagating along the above-described path will be transmitted further within the glass by alternate total internal reflections at the opposite surfaces of the glass, and the intensity of these rays can be detected by means described in greater detail later in the text.

Due to the different effect of deposited dirt on the radiation transmitted through the glass, when the accumulation of dirt on the surface of a plate such as the windshield of a vehicle is to be measured, the radiation employed for the measurement must be transmitted to the opposite direction of that used in the above-described measurement as will be described in greater detail later in this text. In this latter case, the source of radiation is placed so aligned with respect to the surface of the plate that the angle $\beta 2$ of the measuring radiation to the surface of the plate toward the detector element is in the range 0°–90°.

According to a preferred embodiment of the invention, both above-mentioned methods are used simultaneously thus accomplishing the demand-based automatic control system for the windshield wiper and washer equipment of a vehicle, for instance.

The measuring radiation which is transmitted inside of the surface of the plate by reflection at the water and/or dirt particles and by total reflection at the surfaces of the plate is detected by means of a detector means. According to the invention, detection can be implemented in a plurality of different methods. Typically the detector means comprises a detector element sensitive to the measuring radiation combined with elements serving to collect the measuring radiation to the detector means.

According to a simple embodiment of the invention, the detector means is mounted to the surface of a plate at its edge either directly, or alternatively, via a radiation focusing element such as a lens. For instance, in a vehicle the location of the detector means can be, e.g., at one edge of the windshield attached to the surface of the glass thus permitting total visual concealment of the detector means under, e.g., the rubber weatherseal of the windshield. The detector means may also be entirely or partially embedded under the surface of the plate.

According to another embodiment of the invention, the detector means comprises a transducer piece made of a material transparent to the measuring radiation, said transducer piece being attached to a suitable point of the vehicle windshield, whereby the detector means is attached to the outer surface of the transducer piece, or alternatively, mounted inside the transducer piece either directly or via a radiation transmitting element and/or collecting optics. Here, the interface between the transducer piece and the surface of the plate is advantageously provided with an opaque layer having an aperture or window through which the measuring radiation can enter the transducer piece. Transmission of the radiation undergoing total internal reflection into the transducer piece via the window is assured by proper choice of the piece interfacing medium and the material from which the piece is made. The detector means is mounted to the transducer piece at such a point where the detector is illuminated only by the radiation transmitted by total internal reflection in the inside of the plate, while other radiation transmitted through the plate such as background light will be stopped from reaching the detector means. Thus, the background light can be kept apart from the measurement signal, since the radiation undergoing total internal reflection will be incident at an angle to the interface normal which is always larger than the angle of incidence of the radiation entering the plate from outside.

In this embodiment the outer surfaces of the transducer piece with the exception of the above-mentioned window and the location of the detector means are advantageously provided with an inside nonreflecting layer. This layer serves to absorb all other radiation except that intended to illuminate the detector means, whereby this radiation according the considerations given above is invoked only by the water droplets and/or dirt-containing droplets and is transmitted in the inside of the plate by total internal reflection.

According to an advantageous embodiment of the invention, both the radiation source and the detector means can be situated relatively far from the measured object. Hence, the measuring radiation can be transmitted via an optical fiber, for instance. It is also possible to transfer both the measuring radiation to the measured object and the radiation originating from the measuring element such as the transducer piece to the detector means via the same optical fiber.

According to the invention, the measuring radiation is advantageously transmitted at different times from sources of radiation and detected synchronously at corresponding instants of time using a single detector means. In practice, the measuring rays are transmitted in pulses and then detected synchronously with the help of a suitable electronic circuitry by the detector means in order to discriminate from which source of radiation the received rays originate. In this form the apparatus is suited for selective detection of both water and dirt on the windshield of a vehicle, for instance, and then performing a demand-based starting and stopping of the windshield wiper and washer equipment using only a single detector means and principally a common electronic circuitry.

BRIEF DESCRIPTION OF THE DRAWINGS

In the following the invention and its different embodiments are described in greater detail with reference to the annexed drawings in which.

DESCRIPTION OF THE PREFERRED EMBODIMENTS

Figure 1A:
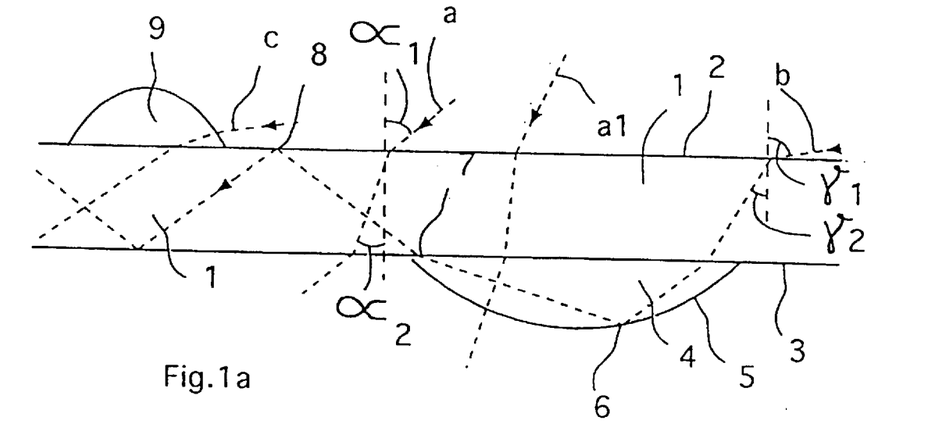
FIGS. 1a and 1b are detailed illustrations of the optical path of the radiation employed for the measurement.

To elucidate the operating principle of the invention, in FIG. 1 is first examined the path of a ray a of radiation incident on a surface 2 of an entirely smooth plate 1 of a constant thickness of radiation-transparent material, whereby the ray may be incident in a random direction from a homogeneous medium surrounding the plate. Although the refractive index of the surrounding medium (e.g., air) is smaller than that of said plate 1, the entering radiation cannot undergo total internal reflection inside the plate 1 at its surfaces 2 or 3, but instead, is transmitted through the plate 1 so that the angle $\alpha 1$ of the incident radiation a to the normal of the interface 2 is equal to the angle $\alpha 2$ of the transmitted radiation a to the normal of the interface 3. With these assumptions, the measuring radiation a is entirely transmitted through the plate 1 and, in accordance with the invention, cannot reach the detector means which is accessible only by radiation transmitted by total internal reflection inside the plate 1.

As shown in FIG. 1a, the ray a1 is transmitted through the plate 1 and a droplet 4 deposited on its surface 3 in the same manner as the radiation a is transmitted through the plate 1 at a point not covered by deposits.

The ray b drawn in the diagram represents the path of the ray employed according to the invention for the purpose of sensing liquid deposits such as a water droplet 4 on the surface 3 of the plate 1. Assuming that air is the ambient gaseous medium in the diagram, glass the material of the plate 1 and water the liquid deposited on the surface 3 of the plate 1, the corresponding values of refractive indices for visible light are: approx. 1.0 for air, approx. 1.5 for glass and approx. 1.3 for water. According to the diagram, when the ray b is incident on the interface 2 between air and glass, the ray entering the glass 1 is refracted so that the angles γ1 and γ2 of the ray incident on the interface 2 and the ray passing through the interface to the normal of the interface 2, respectively, are given by the law of refraction which states that the ratio of the sines of these angles is equal to the inverse ratio of the corresponding refractive indices. Reflection at the next interface 3 (glass-air interface) obeys the same law. When the ray b is incident on the water-air interface 5, the ray travelling along the path drawn in the diagram undergoes total internal reflection at the interface 5 back to the inside of the water droplet, because the angle of the ray b to the normal of the water surface 5 at the point 6 of incidence is larger than the critical angle of total internal reflection. Next, the ray b is refracted again at the water-glass interface 3 at the point 7 according to the law of refraction described above. As the ray is a second time incident on the glass-air interface 2 at the point 8, the ray will be totally reflected back to the inside of the glass on the same grounds as at the water-air interface. Subsequently, the ray will travel inside the glass by a series of total internal reflections alternately at the opposite walls of the glass until reaching the edge of the glass 1, or alternatively, a medium interfacing with the surface of the glass 1, whereby the refractive index of the medium must be sufficiently high to allow the ray to escape the glass. Such a medium can be, e.g., the material of a transducer piece and the mounting medium of the piece.

In FIG. 1a the ray c is drawn to be first incident on a water droplet 9 at its entrance into the glass. The ray obeys the law of refraction at the air-water and water-glass interfaces and is then totally reflected at the glass-air interfaces 3 and 2 on the same grounds as described for the ray b above. Thus, such a path facilitates the sensing of water also on that side of the glass from which the measuring rays are transmitted.

Figure 1B:
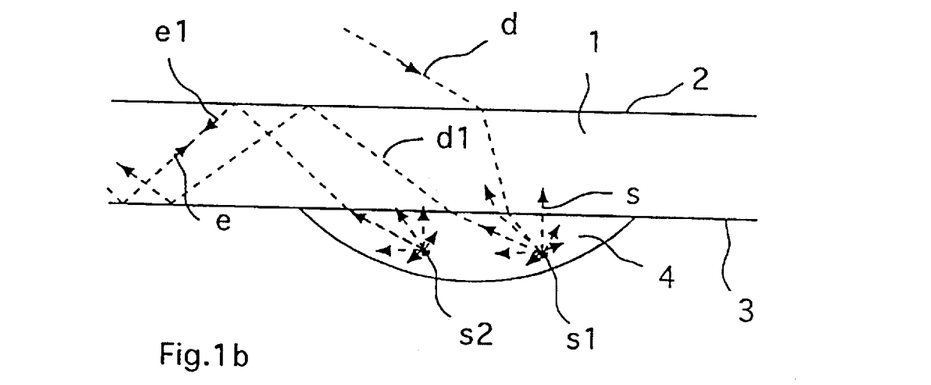

In FIG. 1b the application of the method according to the invention is elucidated for the sensing of solids embedded in an optically suitable medium deposited on the surface of the plate 1. Such solids occur in dirt droplets usually in the form of small particles or as an uneven layer of solids. For greater clarity, the diagram illustrates only two solid particles s1 and s2 in liquid 4 deposited on the surface 3 of the plate 1. Next, the scatter angles of radiation impinging on these particles are examined. The intensity of radiation d scattered by a particle s1 is illustrated with by the different lengths of arrows drawn in different directions representing the scattered rays s. From theoretical considerations it is known that for a large number of very small particles, the intensity of scattered radiation is strongest in the very opposite direction of the incident radiation and, as a function of the scattering angle, falls rapidly in directions deviating from this backward direction. In FIG. 1b the path of one such ray d1 scattered by particle s1 is drawn, whereby the ray is shown to travel by total internal reflection in the inside of the plate 1 almost exactly reverse to the entrance direction of the ray. After backscattering, this ray d1 follows exactly the same path as the ray b in FIG. 1a. The amount of solids can be sensed by detecting the intensity of such radiation. The radiation e incident on the solid particle s2 is scattered in the same manner as described above for the radiation d. The only difference herein is that prior to backscatter, the travel of the radiation e takes place along the inside of the plate 1 by total internal reflection at the surfaces 2 and 3. Alternatively, the entering ray may be incident on a solid particle prior to undergoing any total reflection at the inside surface of the plate 1. The backward oriented point of arrow denotes a backscattered ray e1 travelling in the opposite direction of the entrance of the ray e. In fact, the intensity of scatter is strongest in this reverse direction. The latter example is representative of the embodiment of the invention illustrated in FIG. 4c. The other embodiments of the invention are illustrated by the path of the ray d and its scattering.

Figure 2:
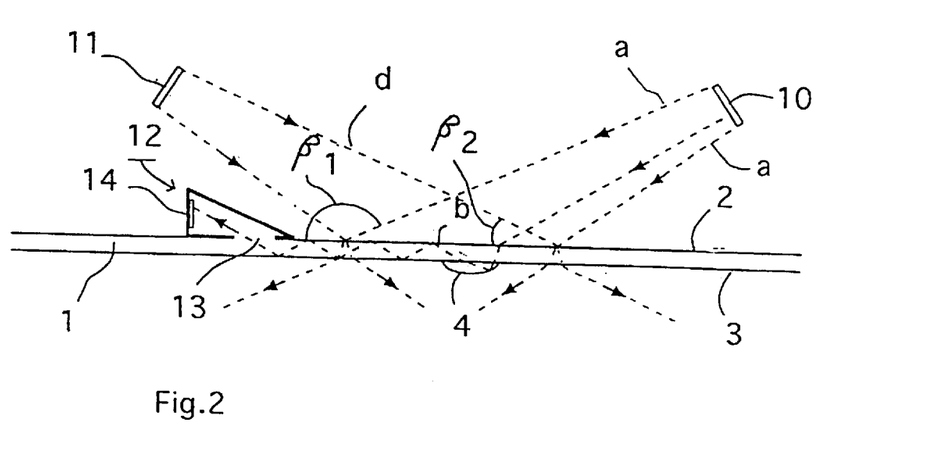
FIG. 2 is a schematic illustration of the measurement method and geometry arrangement according to the invention.

In FIG. 2 two radiation-emitting sources 10 and 11 employed for the measurement are shown aligned at suitable angles to the radiation-transparent plate such as, e.g., the windshield 1 of a vehicle and to the transducer piece 12 adapted to receive the measuring radiation.

As shown in the diagram, radiation is emitted from two separate sources 10 and 11 of radiation to the measured area obliquely through a windshield 1. When the windshield is dry, the radiation emitted by the source 10 continues its travel on the other side of the glass in its original direction. These rays are denoted in the diagram by letter a. When the outer surface of the glass 1 is covered with liquid droplets 4, a fraction of radiation entering the droplets is transmitted through the droplets undergoing refraction as determined by the shape of the droplets. However, another fraction of the radiation incident on the droplets is totally reflected at the interface between the droplet and air. Further, a fraction of this totally reflected radiation returns back to the inside of the glass 1 at an angle to the glass surface that again causes total internal reflection. This fraction of the light continues its path in the inside of the glass 1 by a series of alternate total internal reflections at both of its opposite surfaces 2 and 3 as shown in FIG. 1a.

To the inside surface 2 of the glass 1 is attached a transducer piece 12 by means of a suitable mounting method (using glue, etc.). Further, by a proper selection of the materials for the mounting medium and the transducer piece 12 (that is, adjusting the refractive indices approximately equal to the refractive index of glass), the totally reflected radiation can be made to enter the transducer piece 12. As such totally reflected radiation is incident on the interface at an angle to the normal which is larger than the entrance angle of the radiation entering the glass from its outside, it can be selectively received by means of a suitable window placed between the transducer piece 12 and the glass 1 and by means of proper placement of nonreflective surfaces as described in greater detail in FIG. 3. This results in a radiation signal which is independent of the strongly varying background radiation and has an intensity which is proportional to the amount of water droplets. This signal is detected by means of radiation-sensitive element 14 (detector element) and is amplified. With a sufficient increase in the magnitude of the signal, it is converted into an output signal controlling, e.g., the wipers. The operation of the wipers removes the liquid droplets from the glass surface, and thus the wipers are automatically switched off until the need reappears.

Further, the radiation emitted by a radiation source 11 permits selective detection of solids on the outer surfaces 2 and 3 of the glass 1. When the radiation d is transmitted at the entrance angle shown in the diagram, the same detector element 14 serves to provide a similar function to that described above on the basis of scattering from the solids particles as depicted in FIG. 1b. This arrangement presumes that the solids particles are mixed with a liquid or any other transparent medium deposited on the surface of the glass 1. The information obtained herein can be used for combined automatic control of the windshield washer equipment and wipers according to the same principles as described above for the automatic control of the wipers to remove the water. By transmitting and receiving the pulses of radiation at a high repetition rate alternately at either entrance angle, a continuously operating, selective, automatic control system is achieved for the wiper/washer equipment using only one detector element. By contrast, none of the prior-art inventions have even contemplated the possibility of achieving selectivity.

Figure 3:
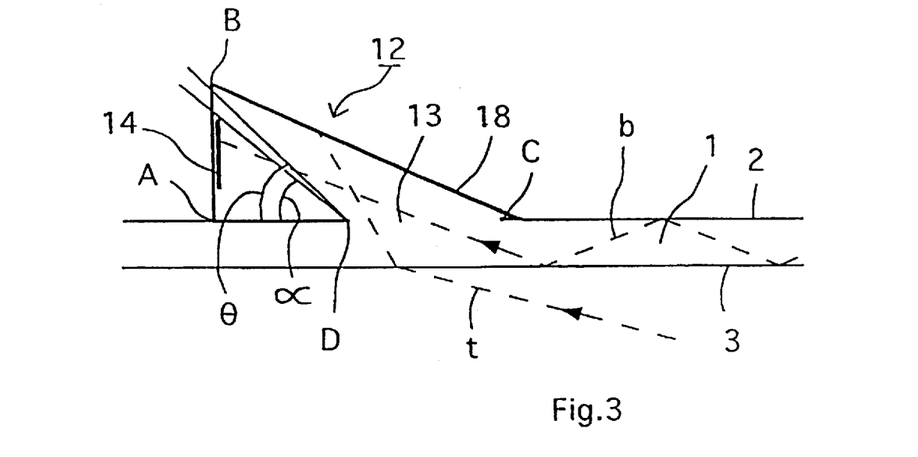
FIG. 3 is a schematic illustration of the reception and detection geometry for the measuring radiation.

In FIG. 3 an embodiment of the detection arrangement for the measuring radiation is shown diagrammatically.

In this arrangement the radiation b with an intensity proportional to the level of the measuring radiation and travelling by total internal reflection inside the glass layer 1 is routed out from the glass. This is achieved by means of a transducer piece 12 attached to the glass. If the refractive indices of the transducer piece 12 and the medium employed in the mounting thereof are properly selected, the radiation can exit from the glass 1 to the transducer piece 12. Advantageously, the materials should have their refractive indices equal or close to that of glass. Differences in the refractive indices will cause the differences between the angles to be described later in the text. If the refractive indices are properly stepped down from layer to layer, total internal reflection at the interface is also possible.

Obviously, the interface between the glass 1 and the transducer piece 12 is also transparent to background radiation t entering from outside the glass 1 with a varying intensity. This disturbing radiation with a widely varying intensity must be discriminated in the transducer piece from the weak measurement signal. Principally, two different methods and/or their combinations are available for this purpose. In one of the methods, the radiation undergoing total internal reflection in the inside of the plate is decoupled out from the plate into a separate transducer piece for detection, while in the other method this radiation is detected using a detector mounted directly inside the plate, or alternative, to the surface of the plate at its edge.

In FIG. 3 the method is illustrated in which the discrimination takes place by means of angle selection and suitable windowing at the interface between the glass 1 and the transducer piece 12. In the diagram is shown a sectional view of the glass 1 with the transducer piece 12 attached thereto. In the illustrated embodiment the transducer piece comprises a piece with a triangular longitudinal section having its corners denoted by letters A, B and C. The side A–C of the transducer piece 12 is attached to the surface 2 of the glass 1. The side A–C of the transducer piece 12 forming the interface between the transducer piece and the glass 1 is coated for the area A–D by a radiation absorbing or reflecting material. Hence, the radiation can pass the interface only through the area D–C which is transparent to radiation and forms a window through which the radiation travelling in the inside of the glass 1 by total internal reflections is decoupled via the transducer niece 12 to the detector 14. The detector element 14 is mounted to the side A–B of the transducer piece. Without departing from the spirit of the invention, the area A–D of the interface can be made either radiation absorbing or reflecting. The latter type of interface has the benefit that the heating effect of, e.g., direct sunshine on the transducer piece 12 remains smaller.

After passing through the window area D–C, the totally reflected radiation representing the measurement signal can travel to the left within the transducer piece in all directions in which it can hit the detector 14. External radiation passing through the transducer piece 12 can be extinguished on the outer surface B–C of the transducer piece 12 with the help of a nonreflective coating placed on the surface. Alternatively, the surface B–C can be left transparent, whereby the background radiation t can freely pass out from the transducer piece 12. In this case the transducer piece must have such a geometry that the (total) reflection of the background radiation from this surface to the detector is impossible. Then, the background radiation is prevented from causing heating of the transducer piece.

The detector 14 is advantageously mounted to the side A–B of the transducer piece 12 so that a line drawn toward the detector 14 from the edge D of the window D–C (denoted by numeral 13) to the top edge of the detector 14 forms with the plate an angle $\alpha$ which is smaller than the critical angle $\theta$ of total internal reflection discussed earlier in the text. This arrangement prevents the background radiation t entering via the window D–C from reaching the detector 14 under any circumstances.

Without departing from the spirit of the invention, the geometry of the transducer piece attached to the glass can be varied as desired provided that the above-described essential preconditions for the selective discrimination of the measuring radiation from the background radiation are fulfilled.

Figure 4A:
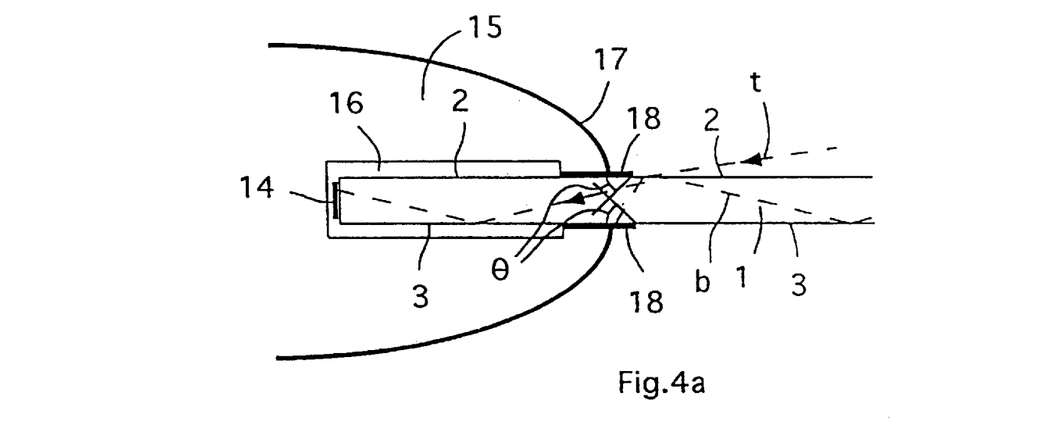
FIGS. 4a, 4b and 4c are schematic illustrations of the measurement geometry arrangements according to the invention.
Figure 4B:
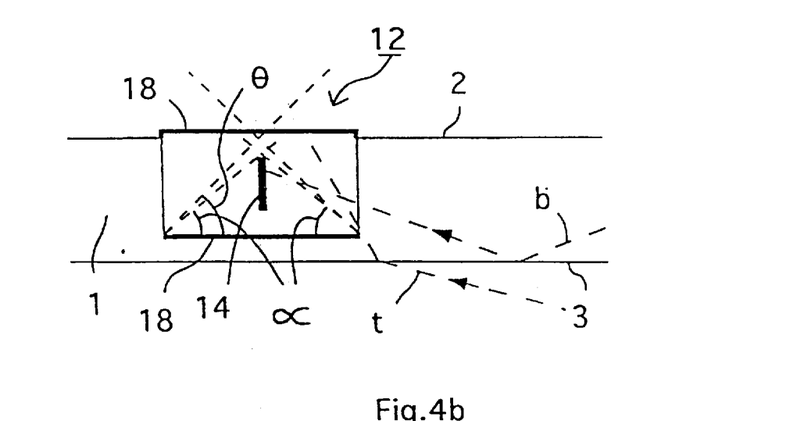
Figure 4C:
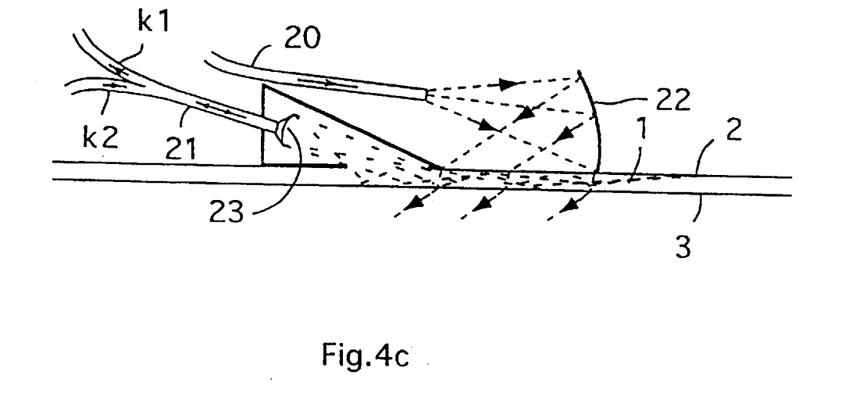

The drawings of FIG. 4 illustrate alternative embodiments of transducer and radiation source arrangements which are based on the operating principle according to the invention, but are optimized for different applications.

In FIG. 4a the detection of the measuring radiation is adapted to the edge of the glass 1, whereby no separate transducer piece is required. In this case, the detector element 14 is mounted under the weatherseal 15 of the glass 1. Then, between the weatherseal 15 and the glass 1 can be provided an air gap 16 which prevents the measuring ray b from passing out from the glass through the surface 2 and becoming absorbed by the rubber weatherseal. Alternatively, the surfaces 2 and 3 of the glass can be provided with a minor coating at the areas covered by the weatherseal 15, whereby the air gap 16 is not mandatory. At the edge 17 of the weatherseal 15, the glass surfaces 2 and 3 are advantageously provided with a radiation absorbing layer 18 serving to prevent the background radiation from propagating by, e.g., reflection at the mirrored surfaces in the inside of the glass 1 up to the detector 14.

In FIG. 4b a transducer piece geometry different from the basic design is shown suited to permit the mounting of the transducer piece 12 either entirely or partially within the inside of the glass 1. However, also the geometry of this variant includes the same angles $\alpha$ and nonreflective surfaces 18 as the basic design serving to shield the detector element 14 against background radiation.

In FIG. 4c an embodiment is shown in which the radiation employed for the sensing of liquid is routed to the point of measurement via an optical fiber 20 and the measuring radiation is analogously with FIG. 3 transferred from the transducer piece 12 via another optical fiber 21 to a remote-located detector element (not shown). In detail, the measuring radiation is passed via an optical fiber, e.g., a glass fiber 20 to a mirror 22 which reflects the radiation in the direction of the transducer piece 12 onto the surface 2 of the plate 1. The geometry and function of the transducer piece 12 is similar to that illustrated in FIG. 3 with the exception that herein the piece is complemented with a radiation collecting element, e.g., a lens 23 from which the measuring radiation is passed along an optical fiber 21 further to the detector element (not shown). The mirror 22 may be omitted if the fiber 20 is aligned to transmit the radiation directly in the correct direction. The embodiment described above permits easy assembly of the components into a compact package.

Also shown in the diagram is an alternative embodiment in which the fiber 21 is branched into two fibers k1 and k2. Here, the measuring radiation employed for detecting the solids is not taken onto the surface 2 of the plate via an air gap as in the basic embodiment, but rather, via the optical fiber branch k2 and the transducer piece 12, and in fact, so as to transmit the measuring radiation from a direction which is exactly opposite to the direction of the radiation returning via the optical fiber branch k1 as the measurement signal. Because the intensity of the scattered radiation is strongest in the opposite direction of the impinging radiation, this arrangement provides maximum sensitivity.

When desired, the above-described embodiment offers the possibility of optimizing the location of both the detector element and the electronics circuitry with regard to the ambient operating conditions and manufacturing the unit in a compact size.

The electronic circuitry for the automatic control of the wiper/washer equipment may incorporate the transmit/receive sections of the pulsed radiation and pulse amplitude measurement, complemented with the control of the wipers and washer equipment. Such functions can be readily implemented using conventional techniques.

To those versed in the art it is obvious that the invention is not limited by its application to vehicles nor by the embodiment illustrated in the foregoing description and drawings, but rather, can be varied within the spirit and scope of the appended claims. The materials mentioned in the text are given as examples suited to elucidate the principle of the invention and describe its major application. For example, the medium (e.g., a glass in the exemplifying embodiment) need not necessarily have constant thickness provided that the preconditions of total internal reflection are fulfilled. For simplicity, the description of the diagrams above is based on the assumption that the refractive index of the transducer piece is equal to that of the surface of the plate, while this need not be true for the function of the invention.

I claim:

1. A method of detecting liquid and/or solid dirt on the surface of a transparent plate (1), in which method radiation emitted from a source (10, 11) of electromagnetic radiation and is received by at least one detector means (14) sensitive to said electromagnetic radiation, whereby the presence of liquid and/or dirt on the surface (2, 3) of said transparent plate (1) is detected in the form of an intensity change of the radiation received by said detector means (14), comprising (a) placing said source (10, 11) of radiation relative to the surface (2) of said plate (1) so that the radiation emitted by the source is incident via a gas-phase medium on the measured area of the surface of the plate (1), whereby the radiation is transmitted through the plate (1) to air without reflection when the plate is dry and/or clean, but a fraction of the radiation
        (i) undergoes refraction from liquid droplets deposited on the plate on the same side (2) as said source of radiation, or
        (ii) undergoes total reflection from liquid droplets (4) deposited on the surface (3) of the plate on the opposite side from said source of radiation, or
        (iii) is scattered by droplets of radiation-transparent medium containing solid particles deposited on the surface of the plate,
    so as to make said fraction(s) of the radiation enter the inside of the plate (1),
    (b) transferring said fraction(s) of radiation due to presence of liquid and/or solid particles, in the inside of the plate (1) by total internal reflection to the detector means (14), and
    (c) detecting said fraction of radiation as an increase in the intensity of the radiation.

2. A method as defined in any of claim 1, wherein the detector means (14) comprises a transducer piece (12) which is made of a transparent material and has a detector element (14) attached to it, and which detector means is mounted at a suitable point either on the surface (2) of the plate or so as to be partially or entirely embedded inside the plate (1), whereby a fraction of the radiation travelling by total internal reflection in the inside of the plate (1) can exit from the plate (1) into the transducer piece (12) and further pass through the piece to the detector element (14).

3. A method as defined in claim 2, wherein a nontransparent interface between the transducer piece (12) and the plate surface (2) is provided with a transparent window (13) and the detector element (14) is aligned with respect to the window (13) of the transducer piece (12) so that only the radiation travelling by total internal reflection in the inside of the plate (1) can reach the detector (14).

4. A method as defined in claim 2, wherein the radiation from the source of radiation to the point of measurement and/or the radiation from the transducer piece (12) to the detector element (14) are transmitted via an optical fiber (20, 21).

5. A method as defined in claim 4, wherein the measurement is performed using a branched optical fiber (21) so that the radiation used for detecting the presence of solid dirt is transmitted to the point of measurement via the same optical fiber as is used for taking the measuring radiation from the transducer piece (12) to the detector element (14).

6. A method of detecting liquid and/or solid dirt on the surface of a transparent plate (1), in which method radiation emitted by at least one source (10, 11) of electromagnetic radiation is transmitted to propagate in the form of radiation undergoing total internal reflection in the inside of said plate (1) and is received by at least one detector means (14) sensitive to said electromagnetic radiation, whereby the presence of liquid and/or dirt on the surface (2, 3) of said transparent plate (1) is detected in the form of an intensity change of the radiation received by said detector means (14), wherein said source (10, 11) of radiation is placed relative to the surface (2) of said plate (1) so that the radiation emitted by the source is incident via a gas-phase medium on the measured area of the surface of the plate (1), whereby the radiation is transmitted through the plate (1) without reflection when the plate is dry and/or clean while a fraction of the radiation undergoes refraction from liquid droplets deposited on the surface (2) of the plate and/or undergoes total reflection from liquid droplets (4) deposited on the surface (3) of the plate and/or is scattered by droplets of radiation-transparent medium containing solid particles deposited on the surface of the plate, so as to make said fraction(s) of the radiation enter the inside of the plate (1), and said fraction(s) of radiation is/are transferred in the inside of the plate (1) by total internal reflection at the surfaces (2, 3) of the plate to the detector means (14), said fraction of radiation is detected from the intensity increase of the radiation, and wherein (a) the measuring radiation is emitted by two different sources of which one source (10) of radiation employed for detecting the liquid component is so aligned that the angle $\beta1$ of the measuring ray to the plate surface (2) toward the detector means (14) is in the range 90°–180°, while the other source (11) of radiation employed for detecting the presence of solid particles is so aligned that corresponding angle $\beta2$ is in the range 0°–90°, or, alternatively, (b) the radiation employed for detecting the presence of solids is transmitted to the inside of the plate with the help of a transducer piece so as to make the rays propagate inside of the plate at the measured area by total internal reflection at the plate surfaces (2, 3), or (c) the detector means (14) is mounted with respect to said transparent plate (1) so as to receive the radiation propagating by total internal reflection inside of the plate (1) via the surface of the plate at the edge of the plate (1), or (d) the measuring ray is emitted in pulses from two different sources (10, 11) of radiation at different instants of time and is received by a single detector element (14) and the magnitude of the radiation received by the detector element (14) is measured during the pulse or thereafter, whereby selective measurement of both the liquid and solid dirt is accomplished using a single detector element.

7. A method as defined in claim 6, wherein the detector means (14) comprises a transducer piece (12) which is made of a transparent material and has a detector element (14) attached to it, and which detector means is mounted at a suitable point either on the surface (2) of the plate or so as to be partially or entirely embedded inside the plate (1), whereby a fraction of the radiation traveling by total internal reflection in the inside of the plate (1) can exit from the plate (1) into the transducer piece (12) and further pass through the piece to the detector element (14).

8. An apparatus for detecting liquid and/or solid dirt on the surface of a transparent plate (1), in which apparatus radiation emitted by from a source of electromagnetic radiation is detected from an intensity change of reflected radiation, wherein said apparatus has at least one radiation-emitting element (10, 11) placed relative to the surface (2) of the plate (1) so that the radiation emitted by said element is incident via a gas-phase medium on the measurement area of the surface of the plate (1) and the radiation emitted by said element is transmitted through the plate (1) to air without reflection when the plate is dry and/or clean, but a fraction of the radiation (i) undergoes refraction from liquid droplets deposited on the surface (2) of the plate the same side as said radiation emitting element or (ii) undergoes total internal reflection from liquid droplets (4) deposited on the surface (3) of the plate on the opposite side from said radiation element, or (iii) is scattered by droplets of radiation-transparent medium containing solid particles deposited on the surface of the plate, so as to make said fraction(s) of the radiation enter the inside of the plate (1) and become transferred inside of the plate (1) by total internal reflection at its surfaces (2, 3), and said apparatus further has a radiation receiving detector means (14) adapted to receive the radiation travelling inside of the plate (1) by total internal reflection and to detect the fraction of radiation as an intensity increase of the received radiation.

9. An apparatus as defined in claim 8, wherein said radiation receiving means comprise a transducer piece (12), which is made of a material transparent to the measuring radiation and incorporates a detector element (14) attached to it either directly or via a radiation transmitting element (20, 21) and/or a radiation collecting optical system (23), whereby the radiation travelling by total internal reflection in the inside of the plate (1) can exit from the plate (1) into the transducer piece (12) and further pass through the piece to the detector element (14).

10. An apparatus as defined in claim 9, wherein the outer surface of the transducer piece (12) is provided with a nontransparent and from inside nonreflecting layer and that the nontransparent interface between the transducer piece (12) and the plate surface (2) is provided with a transparent window (13) and the detector element (14) is aligned with respect to the window (13) of the transducer piece (12) so that only the radiation travelling by total internal reflection in the inside of the plate (1) can reach the detector (14), whereby the outer surface of the transducer piece (12) as well as the interface between the plate surface (2) and the transducer piece (12) are nontransparent with the exception of the window (13) over such an area that a line drawn from the edge (D) of the window (13) closer to the detector (14) to the top edge of the detector (14) forms with the surface of the plate an angle ($\alpha$) which is smaller than the critical angle ($\theta$) of total internal reflection.

11. An apparatus as defined in claim 8, wherein said apparatus comprises means for emitting the measuring ray in pulses from the source (10, 11) of radiation and means for detecting the magnitude of the measuring radiation received by the detector element (14) during the pulse or thereafter, and means for comparing said magnitude with a predetermined set value.

12. An apparatus as defined in claim 11, additionally comprising means for starting or stopping a windshield wiper based upon deviation of said magnitude from said predetermined set value.

13. An apparatus for detecting liquid and/or solid dirt on the surface of a transparent plate (1), in which apparatus radiation emitted by at least one source of electromagnetic radiation is transmitted inside of said plate (1) in the form of radiation undergoing total internal reflection at the surfaces (2, 3) of said plate, whereby the presence of liquid and/or dirt on the surface (2) and/or the surface (3) of the transparent plate (1) is detected from the intensity change of the totally reflected radiation, wherein said apparatus has at least one radiation-emitting element (10, 11) placed relative to the surface (2) of the plate (1) so that the radiation is transferred from air to the measurement area of the surface of the plate (1) and the radiation emitted by said element is transmitted through the plate (1) without reflection when the plate is dry and/or clean, while a fraction of the radiation undergoes refraction from liquid droplets deposited on the surface (2) of the plate and/or undergoes total internal reflection from liquid droplets (4) deposited on the surface (3) of the plate and/or is scattered by droplets containing solid particles so as to make said fraction(s) of the radiation enter the inside of the plate (1) and become transferred inside of the plate (1) by total internal reflection at its surfaces (2, 3), and said apparatus further has a radiation receiving detector means (14) adapted to receive the radiation travelling in the inside of the plate (1) by total internal reflection and to detect the presence of liquid/dirt deposited on the surface (2) and/or the surface (3) of the plate from the intensity increase of the received radiation, wherein (a) said apparatus comprises two radiation-emitting elements of which one source (10) of radiation employed for detecting the liquid component is so aligned that the angle β1 of the measuring ray to the surface (2) of the plate toward the detector means (14) is in the range 90°–180°, while the other source (11) of radiation employed for detecting the solid particles is so aligned that corresponding angle β2 is in the range 0°–90°, or alternatively, (b) the radiation employed for detecting the presence of solid particles is transmitted to the inside of the plate with the help of a transducer piece so as to make the radiation propagate inside of the plate by total internal reflection at the surfaces (2, 3) of the plate, or (c) said radiation receiving means comprise a radiation-sensitive detector means (14) mounted to the edge of the transparent plate (1), or (d) the measurement is performed using a branched optical fiber (k1, k2) so that the radiation used for detecting solids is transmitted to the point of measurement via the same optical fiber (21) as used for taking the measuring radiation from the point of measurement to the detector element (14).

14. An apparatus as defined in claim 13, wherein said radiation receiving means comprise a transducer piece (12), which is made of a material transparent to the measuring radiation and incorporates a detector element (14) attached to it either directly or via a radiation transmitting element (20, 21) and/or a radiation collecting optical system (23), whereby the radiation traveling by total internal reflection in the inside of the plate (1) can exit from the plate (1) into the transducer piece (12) and further pass through the piece to the detector element (14).

15. An apparatus for detecting liquid and/or solid dirt on the surface of a transparent plate (1), in which apparatus radiation emitted by at least one source of electromagnetic radiation is transmitted inside of the plate (1) in the form of radiation undergoing total internal reflection at surfaces (2, 3) of said plate, whereby the presence of liquid and/or dirt on the surface (2) and/or the surface (3) of the transparent plate (1) is detected from intensity change of totally reflected radiation, wherein said apparatus has at least one radiation-emitting element (10, 11) placed relative to the surface (2) of the plate (1) so that the radiation is transmitted from air to a measurement area of the plate (1) and the radiation emitted by said element (10, 11) is transmitted through the plate (1) without reflection when the plate is dry and/or clean, while a fraction of the radiation undergoes refraction from liquid droplets deposited on the surface (2) of the plate and/or undergoes total internal reflection from the liquid droplets (4) deposited on the surface (3) of the plate and/or is scattered by contaminant droplets so as to make said fraction(s) of the radiation enter the inside of the plate and become transferred inside of the plate (1) by total internal reflection at its surfaces (2, 3), and said apparatus further has a radiation receiving detector means (14) adapted to receive the radiation travelling inside of the plate (1) by total internal reflection and to detect the presence of liquid/dirt deposited on the surface (2) and/or the surface (3) of the plate from the intensity increase of the received radiation, said apparatus comprises means for emitting the measuring ray in pulses from the source (10, 11) of radiation and means for detecting magnitude of measuring radiation received by the detector element (14) during the pulse or thereafter, and means for comparing said magnitude with a predetermined set value, and said apparatus further comprises means for emitting the measuring ray from two sources (10, 11) of radiation in pulses at different instants of time and means for correspondingly receiving the pulses at different instants of time, whereby said apparatus is capable of accomplishing selective detection of both liquid and solid dirt deposited on the windshield of a vehicle, and thus performing demand-based starting and stopping of a windshield wiper and washer.

* * * * *